(12) United States Patent
Fehr et al.

(10) Patent No.: US 9,555,146 B2
(45) Date of Patent: Jan. 31, 2017

(54) METHOD OF STERILIZING AT LEAST ONE OBJECT, STERILIZATION APPARATUS AND USE OF SAME

(71) Applicant: Fresenius Medical Care Deutschland GmbH, Bad Homburg (DE)

(72) Inventors: Thorsten Fehr, Losheim a. See (DE); Franz Kugelmann, St. Wendel (DE); Tobias Veit, Oberthal (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 13/741,675

(22) Filed: Jan. 15, 2013

(65) Prior Publication Data

US 2013/0195717 A1    Aug. 1, 2013

Related U.S. Application Data

(60) Provisional application No. 61/591,414, filed on Jan. 27, 2012.

(30) Foreign Application Priority Data

Jan. 27, 2012  (DE) .................... 10 2012 001 566

(51) Int. Cl.
*A61L 2/20* (2006.01)
*A61B 1/12* (2006.01)
*A61L 2/24* (2006.01)

(52) U.S. Cl.
CPC ............ *A61L 2/208* (2013.01); *A61B 1/125* (2013.01); *A61L 2/24* (2013.01); *A61L 2202/24* (2013.01)

(58) Field of Classification Search
CPC ................................ A61L 2/208; A61L 2/24
USPC ..................................... 422/28, 292
See application file for complete search history.

(56) References Cited

U.S. PATENT DOCUMENTS

| 3,459,184 | A | * | 8/1969 | Ring ................ A61M 25/0111 604/164.08 |
| 4,552,721 | A | | 11/1985 | Fentress et al. |
| 4,943,414 | A | | 7/1990 | Jacobs et al. |
| 5,015,374 | A | | 5/1991 | Mathieu et al. |
| 5,534,221 | A | * | 7/1996 | Hillebrenner ............ A61L 2/26 206/438 |
| 5,556,607 | A | | 9/1996 | Childers et al. |
| 5,869,000 | A | | 2/1999 | DeCato |
| 5,871,692 | A | | 2/1999 | Haire et al. |
| 6,589,481 | B1 | * | 7/2003 | Lin ..................... A61L 2/14 422/20 |
| 2005/0260097 | A1 | | 11/2005 | Williams et al. |

(Continued)

FOREIGN PATENT DOCUMENTS

| DE | 28 18 146 | 11/1979 |
| DE | 35 15 665 | 5/1986 |

(Continued)

*Primary Examiner* — Sean E Conley
(74) *Attorney, Agent, or Firm* — Jacobson Holman, PLLC

(57) ABSTRACT

A method of sterilizing an object having at least first and second openings toward an inner space of the object includes connecting the first opening to a feed line for a sterilization agent, connecting the second opening to an outlet line for the sterilization agent, and conducting the sterilization agent through the feed line into the inner space, through the inner space, and out of the inner space through the outlet line.

19 Claims, 2 Drawing Sheets

(56) References Cited

U.S. PATENT DOCUMENTS

2006/0005841 A1\* 1/2006 Anderson ......... A61M 16/0463
                                                        128/207.14
2009/0261038 A1   10/2009 Heim
2010/0076082 A1\*  3/2010 Gamet et al. ................. 514/557

FOREIGN PATENT DOCUMENTS

| DE | 38 25 573       | 2/1990  |
|----|-----------------|---------|
| DE | 198 27 442      | 12/1998 |
| DE | 10 2005 035 528 | 2/2007  |
| DE | 10 2009 026 377 | 2/2011  |
| EP | 0 452 780       | 10/1991 |
| EP | 1 175 230       | 1/2007  |
| GB | 2 105 591       | 3/1983  |
| WO | WO 2012/003962  | 1/2012  |

\* cited by examiner

METHOD OF STERILIZING AT LEAST ONE OBJECT, STERILIZATION APPARATUS AND USE OF SAME

CROSS-REFERENCE TO RELATED APPLICATIONS

This application claims the benefit of U.S. provisional application No. 61/591,414, filed Jan. 27, 2012, which has a priority of German no. 10 2012 001 566.6 filed Jan. 27, 2012, hereby incorporated by reference.

BACKGROUND OF THE INVENTION

1. Field of Invention

The present invention relates to a method of sterilizing at least one object, to a sterilization apparatus and to a use of same.

2. Description of the Prior Art

Sterilizing methods using ozone are already known from the prior art, for example from EP 1 175 230 B1, in which blood hose systems are sterilized in outer packaging in a sterilization chamber having process steps of evacuation and gassing in ozone as a sterilization agent.

The long sterilization times, the expensive outer packaging and the problems which accompany a controlled vapor phase in the sterilization chamber prove to be disadvantageous here. In this respect, a condensation and drying up namely frequently results due to the pressure fluctuations in the sterilization chamber, which prevents a defined sterilization atmosphere in the sterilization chamber.

Furthermore, methods are known from the prior art in which the sterilization agent is conducted through apparatus having sterilization zones which are difficult to reach. For example in U.S. Pat. No. 4,943,414 a vessel having a vaporizable sterilization agent is connected to the lumen of such an apparatus, with the sterilization agent subsequently being conducted through the lumen by application of a negative pressure.

Such processes are also frequently used for sterilizing endoscopes and similar apparatus, for example. Since such apparatus have to be sterile both internally and externally, only one end of the hollow space or of the lumen is connected to a flow means line of the sterilization agent here, such as can be seen, for example, from DE 198 27 442 A1, so that the sterilization agent can also sterilize the outside of the apparatus after passing through the lumen.

Furthermore, it is known from the prior art, for example, to dispense with the use of outer packaging for apparatus to be sterilized in that such apparatus such as hose systems or medical cassette systems are closed under sterile conditions in the sterilization chamber by means of closing caps. Examples for such closing caps are known, for example from DE 28 18 146 A1, DE 38 25 573 A1 and DE 35 15 665 C1.

SUMMARY OF THE INVENTION

It is therefore the object of the present invention to further develop a method of sterilizing at least one object, a sterilization apparatus and a use of same in an advantageous manner, in particular such that objects having sterilization zones which are difficult to reach can be sterilized simply and reliably.

This object is achieved in accordance with the invention by a method of sterilizing as described herein. Provision is accordingly made that in a method of sterilizing at least one object, with the object having at least two openings toward an inner space of the object to be sterilized, at least one opening is connected to a feed line for sterilization agent and the at least one second opening is connected to an outlet line for sterilization agent and the sterilization agent is conducted through the feed line into the inner space and through the inner space and leaves the inner space through the outlet line.

Such an object which is to be sterilized can in particular represent apparatus having sterilization zones which are difficult to reach such as blood hose systems having longer lumens or combinations of blood hose systems with cassettes or filters.

The advantage results from the method in accordance with the invention that a simple and reliable sterilization possibility is provided, with very short sterilization times simultaneously being possible. It is in particular possible to allow a direct drying and blowing out of the residual gases after the sterilization. Since the inner space which is to be sterilized allows by the connection to the feed line and the outlet line for the sterilization agent that the total inner space of the object can be flowed through by the sterilization agent, it is also possible to set humidity, temperature and sterilization agent and thus to carry out a setting of the ideal sterilization conditions independently. It is also no longer necessary to use a complex and/or expensive apparatus such as a large-volume vacuum chamber for the sterilizing method. A very short exposure of the object to be sterilized to the sterilization agent is possible.

It is conceivable to use a vacuum-tight reception chamber for the sterilization process which can be made simpler and smaller than a conventional vacuum chamber.

A use of ethylene oxide (ETO) can also be dispensed with and it is also not necessary to use gamma rays for the sterilization so that there is also no material damage as a consequence of the effect of rays. Furthermore, the method of sterilizing in accordance with the invention allows a special pretreatment or post treatment of the object which is to be sterilized to be dispensed with.

Provision can furthermore be made that the sterilization agent contains hydrogen peroxide at least in part. The use of hydrogen peroxide advantageously allows a particularly gentle, but nevertheless effective, sterilization to be carried out. Furthermore, the use of hydrogen peroxide simultaneously allows a rapid sterilization of the object to be sterilized.

Provision can in particular be made that the hydrogen peroxide is used in vapor form and/or is introduced into the object in vapor form.

The sterilization agent can consist of hydrogen peroxide or comprise hydrogen peroxide.

It is possible that the hydrogen peroxide is vaporized under environmental pressure and is introduced into the object using a carrier agent at a certain temperature, with the carrier agent preferably being air, in particular sterile air.

It is furthermore possible that the temperature of the sterilization agent is in the range between approx. 40° C. to approx. 100° C. The temperature can in this respect be selected in dependence on the application area and can in this respect amount, for example, to 40° C., 50° C., 60° C., 70° C. or 80° C. It is generally possible to select all values from the range between 40° C. to 100° C.

Provision can moreover be made that the process duration of the sterilization method is selected as between approx. 3 to approx. 20 minutes. Provision can in particular be made that the process duration of the sterilization method is approx. 5 minutes, or also longer, and preferably is less than 20 minutes.

It is furthermore conceivable that the opening or openings connected to the outlet line and/or the opening or openings connected to the feed line is/are sealed in germ-tight manner after completion of the sterilization method.

It hereby advantageously becomes possible to be able to dispense with an outer packaging. In this respect, the fact can be used that objects only to be sterilized in the inner space do not have to be sterilized at the outer side and it is thus sufficient to seal the openings of the object in germ-tight manner after completion of the sterilization method. Such a sealing generally takes place under sterile conditions.

Provision can advantageously be made that the germ-tight sealing takes place by a closing of closure means attached to the object, with the closure means in particular forming a part of the opening or openings during the sterilization method and preferably being closed after completion of the sterilization.

It is moreover possible that the closure means is/are one or more closing caps or include(s) such.

Provision can be made that the openings allow an inline closure which is realized by a hammer plug. This hammer plug can be opened and closed. The hammer plug is open during the sterilization process and is closed on completion of the sterilization process.

It is alternatively conceivable to realize an inline closure by means of a septum. In this respect, a septum which is pushed through by a hypodermic needle is used instead of the closure cap with a hammer plug. Hydrogen peroxide vapor can thus, for example, be introduced through the needle, with the septum then being able to close automatically after completion of the sterilization process when the needle is withdrawn.

It is also conceivable to provide a sterilization chamber having an integrated cap closure apparatus, with the object to be sterilized, such as a hose system, being coupled to the sterilization unit and with a closing, turning the closure cap closed, taking place within the likewise sterilized coupling unit after the sterilization.

A further possibility of closure as part of the germ-tight sealing of the object can take place in that the closure cap is welded closed or is welded off and is hereby closed after completion of the sterilization process. Alternative closure possibilities can also be realized, for example, by the use of sterile membranes, shrink-on hose or the like.

Provision can preferably be made that the method is carried out at least partly under vacuum. It can advantageously be prevented by the partial carrying out of the method under vacuum that a collapse of the object, such as a medical hose system, can occur.

It is furthermore advantageously possible that the object to be sterilized is a medical hose kit, in particular a blood hose system, a medical cassette system or a medical filter, in particular a dialyzer, or comprises a medical hose kit, in particular a blood hose system, a medical cassette system or a medical filter, in particular a dialyzer.

The present invention furthermore relates to a sterilization apparatus for sterilizing at least one object having the features described herein. Provision is accordingly made that in a sterilization apparatus for sterilizing at least one object, wherein the sterilization apparatus has at least one feed line and at least one outlet line for a sterilization agent, wherein the object has at least two openings toward an inner space of the object to be sterilized, it is adapted such that at least one first opening can be connected to a feed line for a sterilization agent and that the at least one second opening can be connected to an outlet line for sterilization agent and that the sterilization agent can be conducted through the feed line into the inner space and through the inner space and wherein the sterilization agent can be led out of the inner space via the outlet line.

For this purpose, the sterilization apparatus has means by means of which the sterilization agent can be conducted through the feed line into the inner space and through the inner space and by means of which the sterilization agent can be conducted out of the inner space via the outlet line. These means can, for example, be pump elements or other conveying elements such as a pressure supply or a supply of an assisting gas.

Provision can moreover be made that the sterilization apparatus has at least one overpressure supply, at least one reservoir for receiving the sterilization agent, at least one valve element, at least one carrier medium supply and at least one heating element by means of which the sterilization agent, in particular the hydrogen peroxide, can be vaporized under environmental pressure and can be introduced at a certain temperature into the object, wherein the carrier medium is preferably air, in particular sterile air, and wherein the carrier medium supply is preferably a sterile air supply.

It is furthermore conceivable that a method as described herein can be carried out using the sterilization apparatus, wherein the sterilization apparatus preferably has a control and/or regulation means by means of which the sterilization apparatus can be controlled and/or regulated such that the method in accordance with one of the claims 1 to 11 can be carried out and/or such that the pressure and/or temperature and/or compositions of the sterilization agent can in particular be controlled and/or regulated by means of the control and/or regulation means.

The present invention moreover relates to the use of a method of sterilizing an object as described herein. Provision is accordingly made that a method and a sterilization apparatus as described herein are used for sterilizing at least one object, in particular for sterilizing a medical hose kit, in particular a blood hose system, a medical cassette system or a medical filter, in particular a dialyzer.

The present invention furthermore relates to a system having the features described herein. Provision is accordingly made that a system includes at least one sterilization apparatus as well as at least one object to be sterilized by the sterilization apparatus, wherein the sterilization apparatus has at least one feed line and at least one outlet line for sterilization agent, wherein the object has at least two openings toward an inner space of the object to be sterilized, wherein at least one first opening is connected to a feed line for a sterilization agent and wherein the at least one second opening is connected to an outlet line for a sterilization agent and wherein the sterilization apparatus has means by means of which the sterilization agent can be conducted through the feed line into the inner space and through the inner space and by means of which the sterilization agent can be conducted out of the inner space via the outlet line.

BRIEF DESCRIPTION OF THE DRAWINGS

Further details and advantages of the invention will now be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
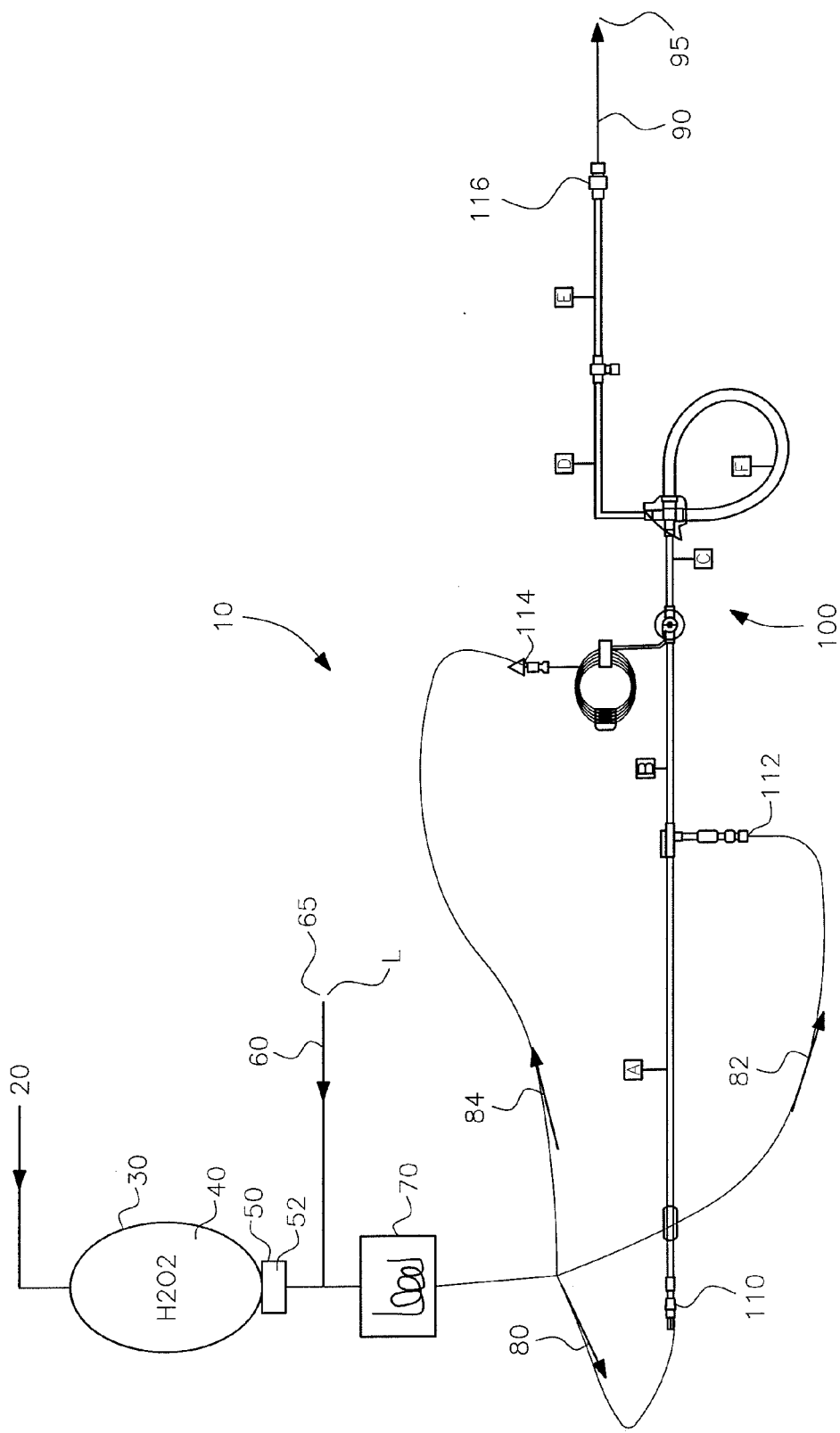
FIG. 1: a schematic view of the sterilization apparatus in accordance with the invention with a connected hose kit to be sterilized.

FIG. 1 shows the schematic structure of the sterilization apparatus 10 in accordance with the invention by means of which a blood hose system 100, as an object to be sterilized having a sterilization zone which is difficult to reach, is sterilized. The sterilization apparatus in this respect has an overpressure supply 20 which is connected to the reservoir 40 for receiving the sterilization agent 40 which is hydrogen peroxide here. A needle valve 52 via which the outflow of the sterilization agent can be regulated is located as a valve element 50 at the outlet side of the reservoir 30.

The connection of the carrier medium supply 60 takes place downstream of the needle valve 52, with sterile air L being supplied as the carrier medium 65 here. A heating 70 is located downstream of the carrier medium supply 60 so that hydrogen peroxide present in vapor form at this point can be introduced into the object 100 at a certain temperature with the sterile air as a carrier medium. In this respect, the temperature of the sterilization agent is in the preferred range from approx. 40° C. to approx. 80° C., here at approx. 60° C. The sterilization agent is fed via the feed lines 80, 82, 84 to the openings 110, 112 and 114 of the medical hose kit 100 which is to be sterilized so that the sterilization agent can flow through all parts of the lumen of the hose kit 100. The sterilization agent leaves the hose kit via the opening 116 and flows via the line 90 into the condenser 95 of the sterilization apparatus 10.

The sterilization method consequently takes place such that the hydrogen peroxide (H2O2) is vaporized and is conducted at a certain temperature with the carrier medium, namely the supplied sterile air L through the object 100 to be sterilized, that is the blood hose system 100 here.

It is generally also conceivable that any object which has sterilization zones which are difficult to reach, for instance a dialysis filter or a medical cassette system with an integrated blood hose system, can be sterilized as the object to be sterilized by the sterilization method or the sterilization apparatus 10.

A sterilization of this object, e.g. of a blood hose system 100, can already be achieved after less than 20 minutes, preferably after less than 5 minutes, which depends, however, on the nature of the object to be sterilized, on a flowing through of the object 100 by a 35% hydrogen peroxide vapor.

The blood hose systems 100 are closed inline after the flowing through by hydrogen peroxide vapor so that the systems are inwardly closed in a hermetic and sterile manner.

Figure 2:
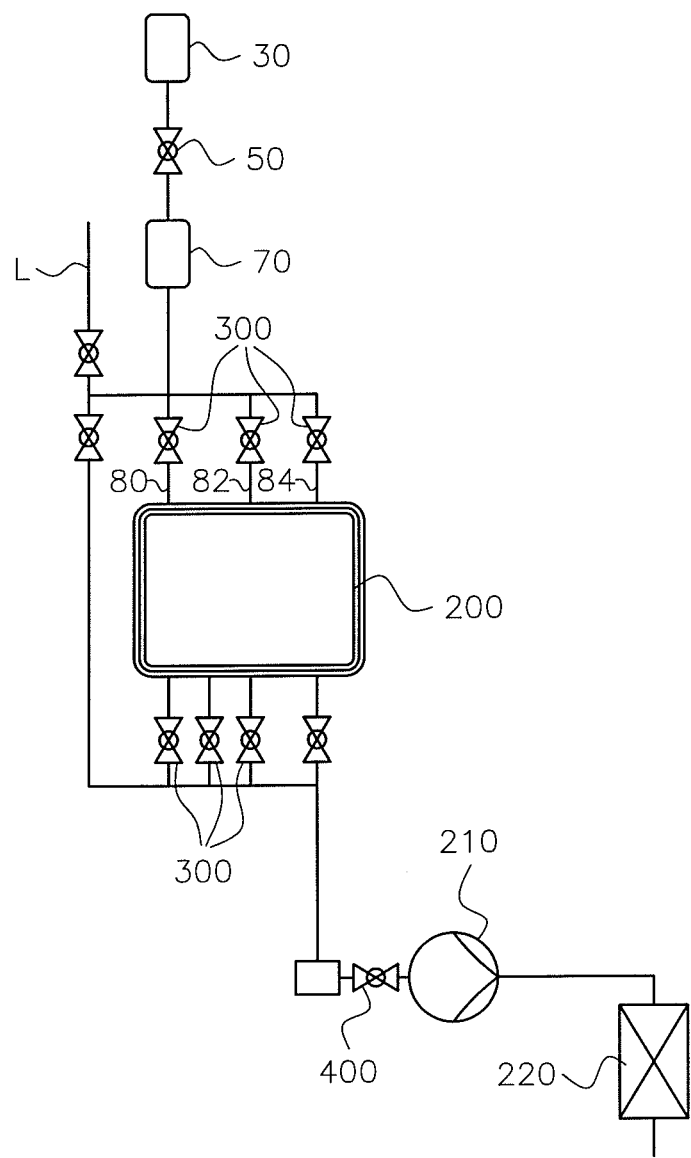
FIG. 2: a further schematic view of the sterilization apparatus in accordance with the invention with a reception chamber for receiving the object to be sterilized.

The arrangement visible from FIG. 2 in which the same components or components of the same function have been provided with identical reference numerals as in FIG. 1 can be used for the method described.

The reception chamber 200 which serves the reception of the object to be sterilized, such as a blood hose system 100, is additionally shown in FIG. 2. Reference numeral 210 characterizes a vacuum pump and reference numeral 220 a destructor for the hydrogen peroxide vapor with an extracted air connection.

As can be seen from FIG. 2, valves 300 are located before and after the reception chamber 200 in the direction of flow of the hydrogen peroxide vapor and can each be closed and opened individually and can be controlled by a control or regulation unit, not shown. Furthermore, a valve 400 is arranged directly upstream of the vacuum pump 210.

Reference symbol L characterizes the option hot air. Hot air can be conducted by the corresponding line system closable by means of one or more valves through the line system upstream and downstream of the reception chamber 200, through the reception chamber 200 itself and also through the line system located before and after the vacuum pump 210 and through the vacuum pump 210 itself. The hot air can be used as the carrier medium for hydrogen peroxide.

In a preferred embodiment of the invention, the sterilization process takes place as follows:

The hose system to be sterilized is preferably connected at all its inlets and outlets to the sterilization apparatus which is shown, for example, in FIG. 2. It is preferred if exactly the same or around the same number of hose ends are used as inlets and as outlets for the sterilization agent.

At the start of the process, the valve 50 between the hydrogen peroxide store 30 and the rest of the system is closed. All other valves are open.

The total system and thus also the reception chamber 200 and the object to be sterilized located therein are evacuated by means of the vacuum pump 210. To prevent any collapse of the flexible hose systems, the reception chamber 200 must likewise be evacuated. The reception chamber 200 is preferably of a smaller and simpler design than vacuum chambers known from the prior art.

In the next step, the valve 50 between the hydrogen peroxide store 30 and the rest of the system is opened. Hydrogen peroxide is vaporized at the evaporator 70 and can flow via the lines 80, 82, 84 into the hose system located in the reception chamber 200 and not shown in FIG. 2. It is possible by different connections of the valves 300 at the reception chamber 200 to flow through specific hose sequences or sequences of the object to be sterilized in a direct manner. This is in particular especially advantageous with hose systems since hoses with very different lumen diameters are contained in such hose systems. Such a procedure increases the security of the method.

In accordance with the present invention, the conditions ideal for the sterilization process with respect to temperature, pressure and sterilization agent can be controlled independently of one another by means of the control and regulation unit, not shown in detail, of the sterilization apparatus which controls and regulates the sterilization procedure.

The hydrogen peroxide can evaporate at lower temperatures than at environmental pressure by the use of the vacuum. If a carrier gas is used, higher temperatures have to be used.

Due to the very short cycle times, preferably of up to 20 min., it is possible to use the sterilization method as an inline sterilization method, that is, for example, as a component of a production line. It is thus conceivable that with such an inline sterilization process the blood hose systems are optionally sterilized directly in the sealing chamber of an outer packaging machine and are packaged together with the outer packaging.

The outer packaging is preferably only used after the sterilization in the present invention. In normal sterilization processes, the outer packaging represents a barrier for the sterilization agent and makes the process more difficult and longer.

Linear systems having a plurality of positions or preferably a so-called "sterilization carousel" can be used as possible embodiments. With such a sterilization carousel, the required switching states can be implemented with the aid of a sliding ring seal in conjunction with the rotation of the carousel.

Generally, a complex apparatus, which moreover has a vacuum chamber, is not necessary. A vacuum chamber or a more simply designed reception chamber can, however, preferably be provided to more simply avoid a collapse of e.g. hose parts, chambers or similar.

Very short sterilization times can be achieved by the direction introduction of the hydrogen peroxide into the lumens of the hose systems. Before the hose systems are removed after the sterilization, they are closed under sterile conditions.

There are different options of a germ-tight sealing for this purpose, as will be explained below:

A first alternative is that the openings allow an inline closure which is realized by a hammer plug. This hammer plug can be opened and closed. The hammer plug is in this respect arranged in a closure cap, for example, which is screwed or placed onto a connector of the hose system in a sealing manner and which can be unscrewed for connecting the connector of the connector system. During the sterilization process, the hammer plug and thus also the closure cap is open and the hammer plug is only moved into the closure position on completion of the sterilization process.

A second alternative is to realize an inline closure by means of a septum. In this respect, a septum which is pushed through by a hypodermic needle is used instead of the closure cap with a hammer plug. Hydrogen peroxide vapor can thus, for example, be introduced through the needle, with the septum then being able to close automatically after completion of the sterilization process when the needle is withdrawn.

A third alternative is to provide a sterilization chamber having an integrated cap closure apparatus, with the object to be sterilized, such as a hose system, being coupled to the sterilization unit and with a closing, turning the closure cap closed, taking place within the likewise sterilized coupling unit after the sterilization.

A further possibility of closure as part of the germ-tight sealing of the object can take place in that the closure cap, e.g. a hose piece of the closure cap, is welded closed or is welded off and is hereby closed after completion of the sterilization process.

Further alternative closure possibilities can also be realized, for example, by the use of sterile membranes, shrink-on hoses or the like.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of sterilizing an object having at least a first opening and a second opening toward an inner space of the object, said method comprising the steps of:

housing the object in a chamber for the sterilization;
physically connecting the first opening to a feed line for a sterilization agent;
physically connecting the second opening to an outlet line for the sterilization agent;
evacuating the object to be sterilized and the chamber in which the object is housed; and
conducting the sterilization agent through the physically connected feed line into the inner space, through the inner space, and out of the inner space through the physically connected outlet line.

2. The method in accordance with claim 1, wherein the sterilization agent at least partly includes hydrogen peroxide.

3. The method in accordance with claim 2, wherein the hydrogen peroxide is at least one of in vapor form and is introduced into the object in vapor form.

4. The method in accordance with claim 3, wherein the hydrogen peroxide is vaporized under environmental pressure and is introduced into the object at a certain temperature by a carrier medium.

5. The method in accordance with claim 1, wherein the temperature of the sterilization agent is in a range of between approximately 40° C. and approximately 100° C.

6. The method in accordance with claim 1, wherein a duration of the method is between approximately 3 and approximately 20 minutes.

7. The method in accordance with claim 1, wherein the first opening physically connected to the feed line and the second opening physically connected to the outlet line are sealed in a germ-tight manner after completion of the sterilization.

8. The method in accordance with claim 7, wherein the germ-tight sealing is effected by a step of closing of a closure element attached to the object during the sterilization method.

9. The method in accordance with claim 8, wherein the closure element includes one or more closure caps.

10. The method in accordance with claim 1, wherein the object to be sterilized is a medical hose kit, a medical cassette system, or a medical filter, or includes a medical hose kit, a medical cassette system, or a medical filter.

11. The method in accordance with claim 1, wherein the object is at least one of a medical hose kit, a medical cassette system, and a medical filter.

12. The method according to claim 4, wherein the carrier medium is air.

13. The method according to claim 12, wherein the air is sterile.

14. The method according to claim 6, wherein the duration of the method is approximately 5 minutes.

15. The method according to claim 8, wherein the closure element forms a part of the at least first and second openings.

16. The method according to claim 8, wherein the closure element is closed after completion of the sterilization.

17. The method according to claim 10, wherein the medical hose kit is a blood hose system.

18. The method according to claim 10, wherein the medical filter is a dialyzer.

19. The method according to claim 1, wherein the step of evacuating the object to be sterilized and the chamber in which the object is housed is effected with a vacuum pump.

* * * * *